United States Patent
Hanagasaki

(10) Patent No.: US 7,731,696 B2
(45) Date of Patent: Jun. 8, 2010

(54) ANTICONTAMINATION COVER

(76) Inventor: Kazuo Hanagasaki, 3-6-8, Ikenokami, Shiroi-Shi, Chiba-Ken (JP)

( * ) Notice: Subject to any disclaimer, the term of this patent is extended or adjusted under 35 U.S.C. 154(b) by 565 days.

(21) Appl. No.: 11/399,556

(22) Filed: Apr. 6, 2006

(65) Prior Publication Data
US 2006/0229566 A1    Oct. 12, 2006

(30) Foreign Application Priority Data
Apr. 12, 2005    (JP) ............... 2005-114649

(51) Int. Cl.
*A61M 25/00* (2006.01)
(52) U.S. Cl. ................................. 604/171
(58) Field of Classification Search ............ 604/171
See application file for complete search history.

(56) References Cited

U.S. PATENT DOCUMENTS

| 5,807,314 | A | 9/1998 | Ross et al. |  |
| 6,527,748 | B1 * | 3/2003 | Suzuki | 604/171 |
| 7,018,373 | B2 * | 3/2006 | Suzuki | 604/528 |
| 2003/0229334 | A1 | 12/2003 | Suzuki |  |
| 2004/0111056 | A1 * | 6/2004 | Weststrate et al. | 604/104 |

FOREIGN PATENT DOCUMENTS

| JP | 2000-126302 | 5/2000 |
| JP | 2003-180840 | 7/2003 |
| JP | 2005-185400 | 7/2005 |
| WO | 03/103566 | 6/2003 |

OTHER PUBLICATIONS

Patent Abstracts of Japan of JP 2003-180840 dated Jul. 2, 2003.
Patent Abstracts of Japan of JP 2005-185400 dated Jul. 14, 2005.

* cited by examiner

*Primary Examiner*—Nicholas D Lucchesi
*Assistant Examiner*—Aarti B Berdichevsky
(74) *Attorney, Agent, or Firm*—Ladas and Parry LLP

(57) ABSTRACT

An anticontamination cover prevents the biotic contamination of a gastrostomy catheter when the gastrostomy catheter is inserted through the mouth into the stomach for percutaneous, endoscopic gastrostomy. The anticontamination cover includes an elongate covering tube having a closed distal end and an open base end, and a loop attached to and projecting from the outside surface of the distal end of the covering tube. An opening is formed in a part of the distal end of the covering tube opposite a part of the distal end to which the loop is attached. A loop of the gastrostomy catheter inserted in the covering tube is passed through the opening of the distal end of the covering tube.

19 Claims, 9 Drawing Sheets

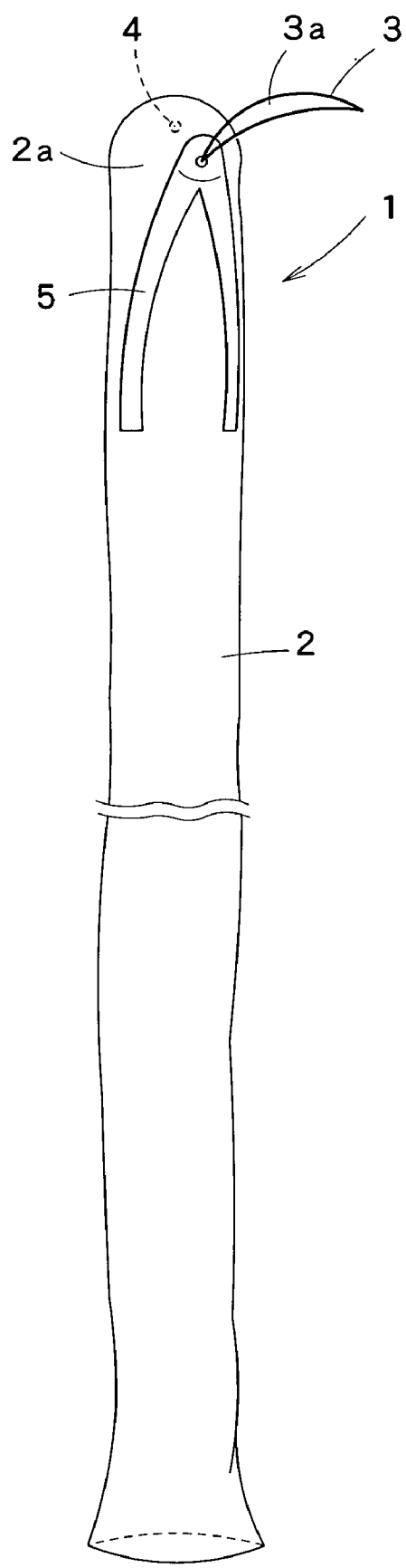
F I G . 1

ANTICONTAMINATION COVER

BACKGROUND OF THE INVENTION

1. Field of the Invention

The present invention relates to an anticontamination cover for covering a catheter for gastrostomy (hereinafter, referred to as "gastrostomy catheter") to protect the gastrostomy catheter from biotic contamination when the gastrostomy catheter is inserted through the oral cavity into the stomach for percutaneous, endoscopic gastrostomy.

2. Description of the Related Art

A gastric fistula is formed through the abdominal wall by percutaneous, endoscopic gastrostomy to give nourishment through the intestine to a patient incapable of oral ingestion. Surgical formation of a gastric fistula by percutaneous, endoscopic gastrostomy is carried out using local anesthetic. A surgical operation for percutaneous, endoscopic gastrostomy can be completed in a short time in the range of 5 to 10 min and the patient recovers in a short period.

Surgical formation of a gastric fistula by percutaneous, endoscopic gastrostomy needs an operation to pass a gastrostomy catheter by way of the mouth, the larynx and the pharynx into the stomach. While the gastrostomy catheter is being passed through the mouth into the stomach, the tube and the dome of the gastrostomy catheter touch the mouth, larynx and pharynx and are contaminated with bacteria.

If a gastric fistula is formed by passing a gastrostomy catheter having a tube and a dome contaminated with bacteria through fistulas formed in the abdominal wall and the gastric wall, the fistulas formed in the abdominal wall and the gastric wall will be contaminated with bacteria. Thus the wounded parts around the fistulas are infected with bacteria and the patient needs to take an antibiotic for a long term to heal the infected, wounded parts. Consequently, gastrostomy takes many days and starting giving nourishment through the intestine is delayed.

An anticontamination cover for protecting a gastrostomy catheter to prevent the infection of wounded parts around fistulas by a gastrostomy catheter is mentioned in JP-A No. 126302 (Patent document 1). This known anticontamination cover covers a gastrostomy catheter entirely to prevent the tube and the dome of the gastrostomy catheter from directly touching the mouth, the larynx and the pharynx to prevent the bacterial contamination of the wounded parts around the fistulas.

This known anticontamination cover includes an elongate tubular bag having opposite open ends, a ligature thread for ligating the open end of the tubular bag, and a cutting thread having strength higher than that of the ligature thread and connected to the ligature thread.

This known anticontamination cover receives a gastrostomy catheter therein with a catheter loop attached to the extremity of the gastrostomy catheter projecting from the open end. The open end from which the catheter loop is projecting is ligated by the ligature thread to prevent the direct contact of the tube and the dome of the gastrostomy catheter held in the tubular bag with the mouth, the larynx and the pharynx.

A knot is formed in the open end of the tubular bag tied by the ligature thread. The knot of the ligature thread is contaminated with bacteria while the gastrostomy catheter covered with the anticontamination cover is passed by way of the mouth, the larynx and the pharynx into the stomach. The tube and the dome of the gastrostomy catheter come into direct contact with bacteria adhering to the knot and are contaminated with bacteria when the knot of the ligature thread is untied and the anticontamination cover is removed from the gastrostomy catheter.

In passing the gastrostomy catheter covered with the known anticontamination cover through the mouth into the stomach, the open end of the anticontamination cover is closed by the ligature thread and a guide wire is connected to the catheter loop attached to the extremity of the gastrostomy catheter. If the knot of the ligature thread closing the open end of the tubular bag is loose, it is possible that the anticontamination cover separates from the gastrostomy catheter and cannot exercise its protective function. Consequently, the tube and the dome of the gastrostomy catheter are contaminated with bacteria.

SUMMARY OF THE INVENTION

The present invention has been made to solve those problems in the related art and it is therefore an object of the present invention to provide an anticontamination cover for covering a gastrostomy catheter, capable of preventing the separation thereof from the gastrostomy catheter and of surely preventing the bacterial contamination of the tube and the dome of the gastrostomy catheter.

The present invention provides an anticontamination cover, for covering a gastrostomy catheter, including: an elongate covering tube having a closed distal end and an open base end; and a loop attached to and projecting from the outside surface of the distal end of the covering tube; wherein an opening is formed in a part of the distal end of the covering tube opposite a part of the distal end to which the loop is attached to pass a loop of the gastrostomy catheter therethrough.

The opening through which the catheter loop of the gastrostomy catheter is passed is formed in the distal end of the covering tube at a position separated from the loop. Therefore, the tube and the dome of the gastrostomy catheter will not come into direct contact with the loop contaminated with bacteria when the gastrostomy catheter is pulled out of the anticontamination cover. Thus the tube and the dome of the gastrostomy catheter can be surely prevented from bacterial contamination.

A guide wire is connected to both the loop of the anticontamination cover and the catheter loop of the gastrostomy catheter. Therefore, the anticontamination cover will not come off the gastrostomy catheter when the gastrostomy catheter covered with the anticontamination cover is inserted by way of the patient's mouth into the patient's stomach. Thus the tube and the dome of the gastrostomy catheter can be surely prevented from bacterial contamination.

BRIEF DESCRIPTION OF THE DRAWINGS

The above and other objects, features and advantages of the present invention will become more apparent from the following description taken in connection with the accompanying drawings, in which:

FIG. 1 is a perspective view of an anticontamination cover in a preferred embodiment according to the present invention;

DESCRIPTION OF THE PREFERRED EMBODIMENTS

Figure 2:
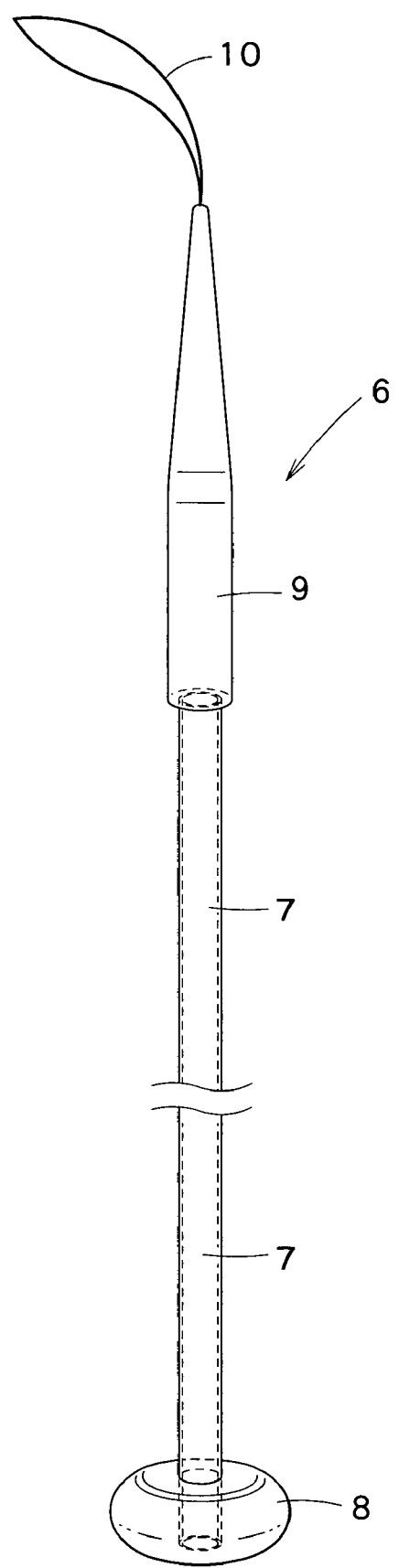
FIG. 2 is a perspective view of a gastrostomy catheter.
Figure 3:
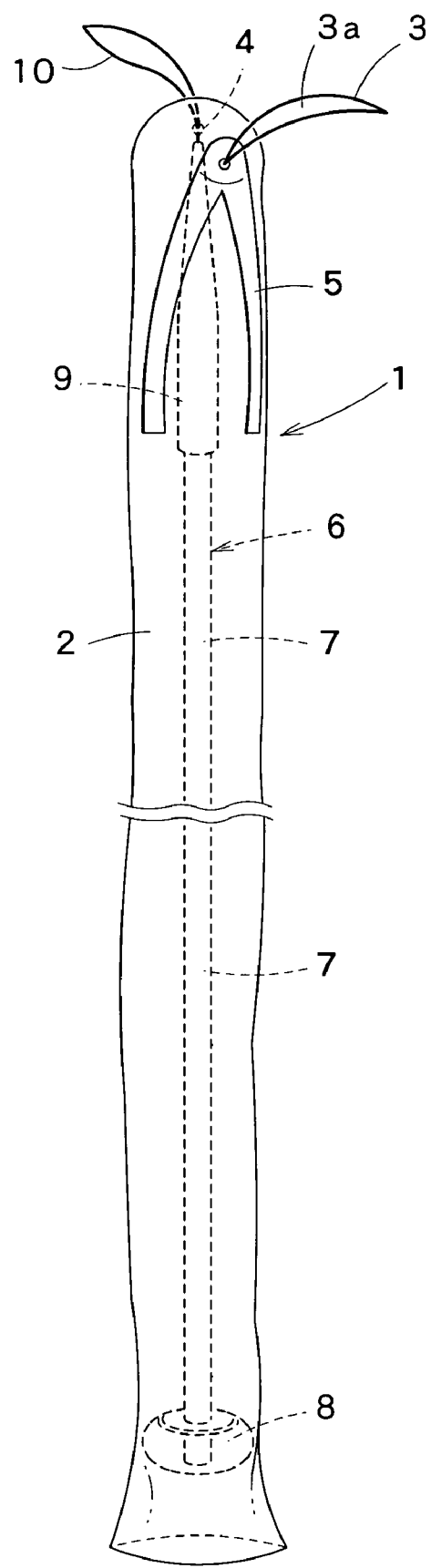
FIG. 3 is a perspective view of the anticontamination cover of the present invention covering the gastrostomy catheter.

FIG. 1 is an abridged perspective view of an anticontamination cover 1 in a preferred embodiment according to the present invention, FIG. 2 is a perspective view of a gastrostomy catheter 6 for percutaneous, endoscopic gastrostomy and FIG. 3 is a perspective view of the anticontamination cover 1 covering the gastrostomy catheter 6.

Referring to FIG. 1, the anticontamination cover 1 of the present invention includes an elongate covering tube 2 having a closed distal end 2a and an open base end, a loop 3 attached to and projecting from the outside surface of the distal end 2a of the covering tube 2 and an adhesive strip 5 attaching the loop 3 to the covering tube 2. An opening 4 is formed in the distal end 2a of the covering tube 2 at a position separated from the loop 3.

The covering tube 2 is formed from a flexible, easily breakable material, such as a vinyl film of a thickness on the order of, for example, 0.03 mm. The covering tube 2 has an overall length of about 70 cm and an inside diameter of about 2.0 cm. The distal end 2a is closed and the base end is open. Preferably, the base end of the covering tube 2 is flared to facilitate inserting the gastrostomy catheter 6 in the covering tube 2. The covering tube 2 is formed from any synthetic resin film other than the vinyl film provided that the covering tube 2 is flexible and easily breakable.

The loop 3 is formed by folding a nylon filament having a diameter of about 0.1 mm and forms an aperture 3a. The nylon filament may be twisted so as to form the aperture 3a.

The adhesive strip 5 is formed in a shape substantially resembling a U-shape and has a back surface coated with an adhesive. The adhesive strip 5 is attached to the outside of the distal end part 2a of the covering tube 2. The adhesive strip 5 may be bonded to the outside surface of the distal end part 2a of the covering tube 2 by welding using a rectangular vinyl film.

Desirably, the opening 4 is formed in the distal end 2a of the covering tube 2 in a diameter big enough to pass a wire loop 10 included in the gastrostomy catheter 6. In FIG. 1, the opening 4 is formed in the distal end 2a of the covering tube 2 opposite to the adhesive strip 5 attached to the covering tube 2 with respect to the center axis of the covering tube 2. However, the opening 4 does not need to be formed in the distal end 2a of the covering tube 2 exactly opposite to the adhesive strip 5 attached to the covering tube 2; the opening 4 may be formed in the distal end 2a at a position separated from the adhesive strip 5. The opening 4 may be a straight slit of a length long enough to pass the wire loop 10 of the gastrostomy catheter 6.

It is desirable that the opening 4 is positioned at a position far enough from the loop 3 so as that the dome 8 does not touch the loop 3 to keep the dome 8 clean when the dome 8 is drawn out from the covering tube 2.

Referring to FIG. 2, the gastrostomy catheter 6 includes a tube 7, a dome 8 formed in one of the opposite ends of the tube 7, a dilator 9 connected to the other end of the tube 7, and the wire loop 10 connected to the dilator 9.

Referring to FIG. 3, the gastrostomy catheter 6 is inserted from the dilator 9 into the anticontamination cover 1. The wire loop 10 is extended outside through the opening 4 formed in the distal end 2a of the covering tube 2 and is extended alongside the loop 3.

Figure 4:
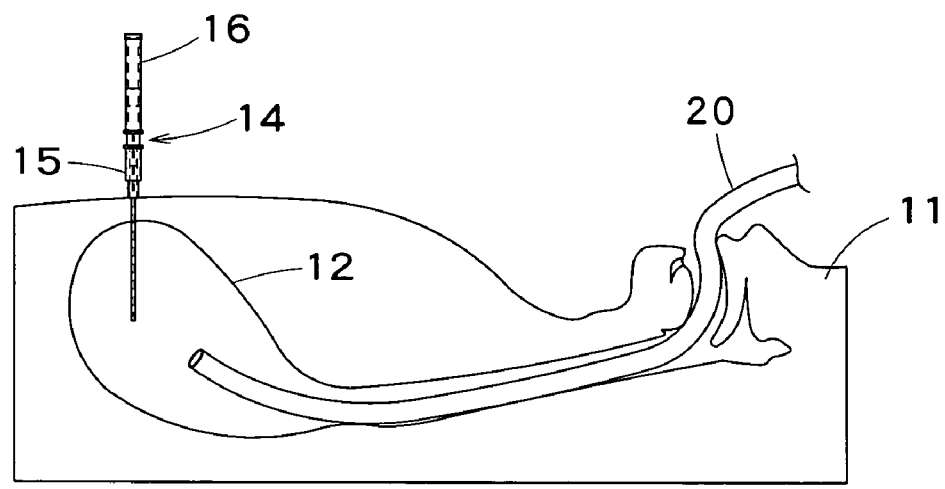
FIG. 4 is a pictorial view showing a state where an endoscope is inserted in the stomach and a sheathed needle is thrust into a holing part during endoscopic gastrostomy.

The use of the anticontamination cover 1 will be explained. To achieve endoscopic gastrostomy, an endoscope 20 is inserted through the mouth of a patient 11 lying on the back into the stomach 12 as shown in FIG. 4. Then, air is supplied through the endoscope 20 into the stomach 12 of the patient 11 to inflate the stomach 12 so that the gastric wall 12a is pressed closely against the abdominal wall 13.

A holing part into which a sheathed needle 14 is to be thrust is determined to determine a position in which a gastric fistula is to be formed. The sheathed needle 14 has a sheath 15 and a needle 16 inserted in the sheath 15. A part around the holing part in which the sheathed needle 14 is to be thrust is anesthetized by local anesthesia. The skin of the holing part is incised in an opening of about 1 cm in length. Then, the sheathed needle 14 is thrust in the incised part.

Figure 5:
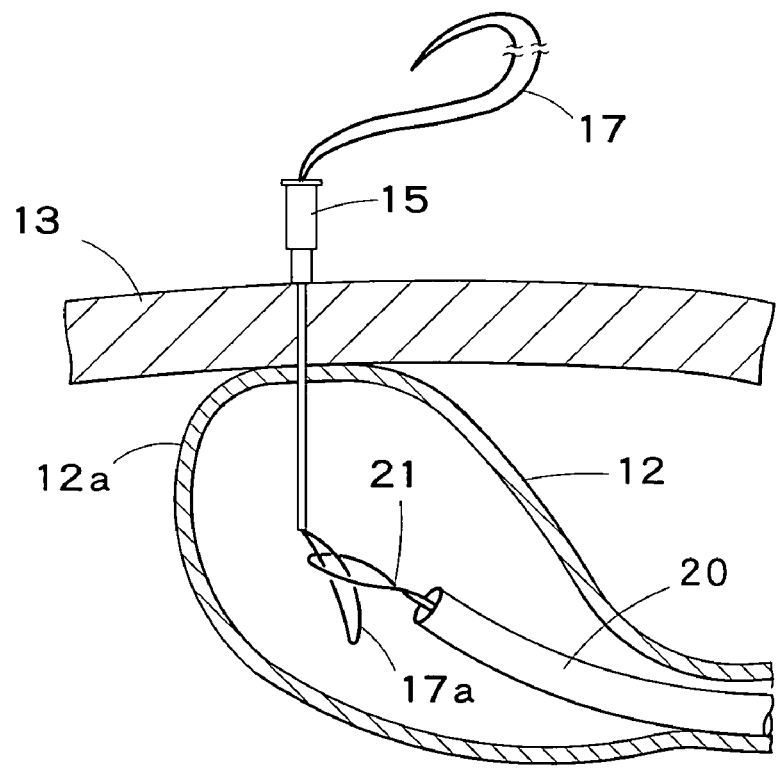
FIG. 5 is a pictorial view showing a state where a guide wire inserted into the stomach has been gripped by a snare forceps during endoscopic gastrostomy.

After the confirmation of the penetration of the sheathed needle 14 through the abdominal wall 13 and the gastric wall 12a, the needle 16 is extracted from the sheath 15. Then, a guide wire 17 having a loop 17a is passed from the loop 17a through the sheath 15 into the stomach 12 as shown in FIG. 5. A snare forceps 21 projecting from the endoscope 20 catches the loop 17a of the guide wire 17 inserted into the stomach 12.

Figure 6:
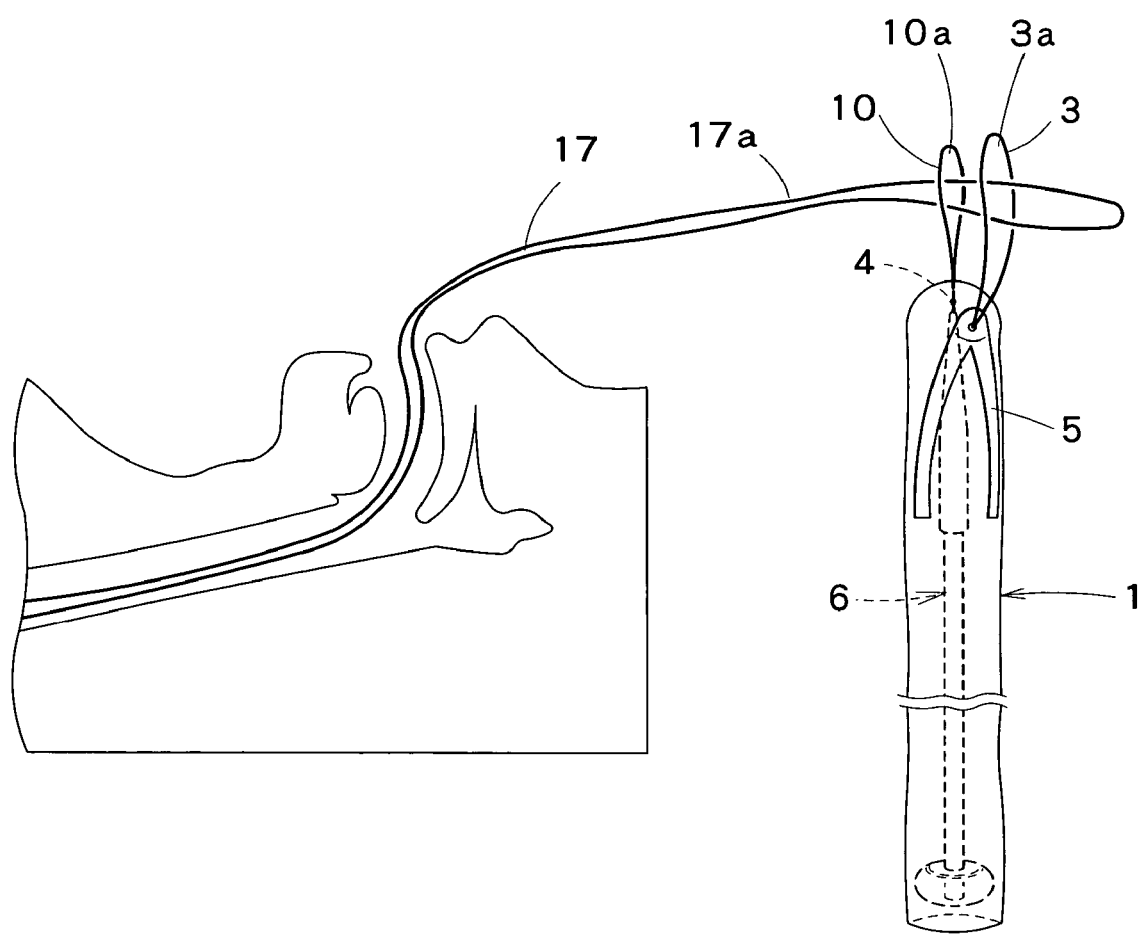
FIG. 6 is a pictorial view showing a state where the loop of the anticontamination cover and the catheter looped of a gastrostomy catheter are inserted in a loop of the guide wire pulled outside the body during endoscopic gastrostomy.

Subsequently, the snare forceps 21 holding the guide wire 17 is pulled outside together with the endoscope 10 through the mouth. Then, the snare forceps 21 releases the guide wire 17. Then, a looped end part 10a of the wire loop 10 of the gastrostomy catheter 6 and a looped end part 3a of the loop 3 of the anticontamination cover 1 are penetrated through the loop 17a of the guide wire 17 as shown in FIG. 6.

Figure 7:
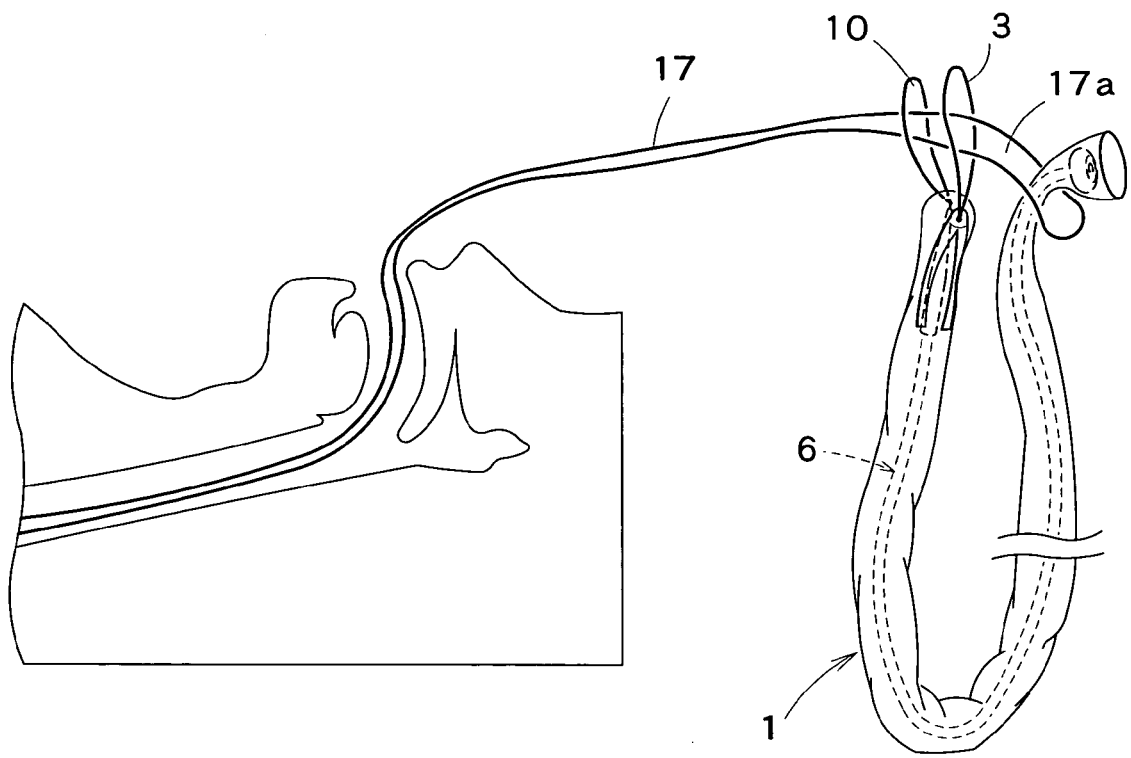
FIG. 7 is a pictorial view showing a state where the anticontamination cover and the gastrostomy catheter have been connected to the guide wire pulled outside the body during endoscopic gastrostomy.

Then, the base end of the anticontamination cover 1 is put through a part, on the outer side of the wire loop 10 of the gastrostomy catheter 6 and the loop 3 of the anticontamination cover 1, of the loop 17a of the guide wire 17 as shown in FIG. 7 and the base part of the anticontamination cover 1 is pulled.

Figure 8:
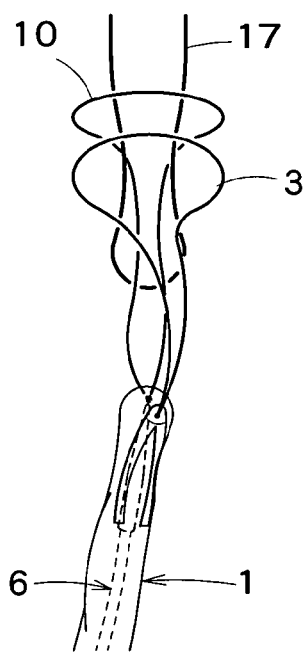
FIG. 8 is a view of a part of FIG. 7.
Figure 9:
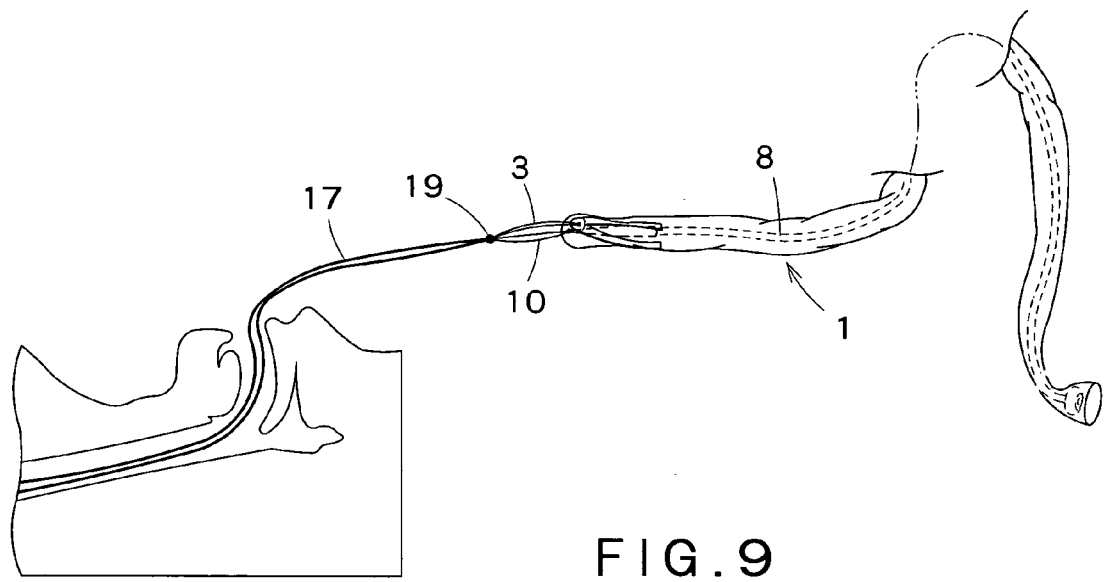
FIG. 9 is a pictorial view showing a state immediately before pulling the anticontamination cover and the gastrostomy catheter into the body during endoscopic gastrostomy.

Consequently, the loop 17a of the guide wire 17, the wire loop 10 of the gastrostomy catheter 6 and the loop 3 of the anticontamination cover 1 are tied in a knot 19 as shown in FIG. 8. Thus both the gastrostomy catheter 6 and the anticontamination cover 1 are connected to the guide wire 17 as shown in FIG. 9.

Figure 10:
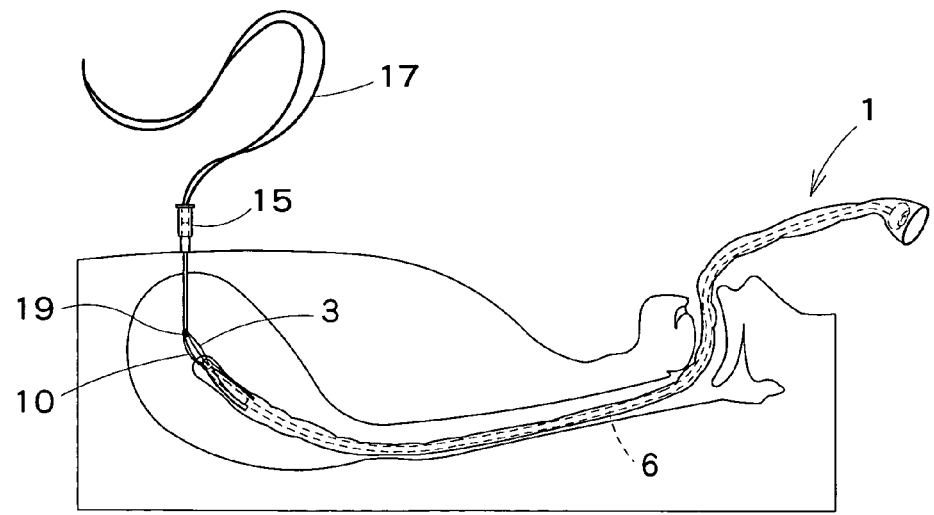
FIG. 10 is a pictorial view showing a state where the anticontamination cover and the gastrostomy catheter have been pulled into the body during endoscopic gastrostomy.

Then, the guide wire 17 extending outside the patient's abdomen is pulled in a direction away from the patient by hand. Consequently, the anticontamination cover 1 covering the gastrostomy catheter 6 and connected to the guide wire 17 is pulled through the mouth, the larynx, the pharynx and the gullet into the stomach 12 as shown in FIG. 10.

At this stage, the gastrostomy catheter 6 is covered with the anticontamination cover 1. Therefore, the tube 7 and the dome 8 of the gastrostomy catheter 6 do not come into direct contact with the mouth, the larynx, the pharynx and the gullet while the gastrostomy catheter 6 is pulled through the mouth, the larynx, the pharynx and the gullet into the stomach 12.

Since both the anticontamination cover 1 and the gastrostomy catheter 6 are connected to the guide wire 17, the anticontamination cover 1 does not separate from the gastrostomy catheter 6 while the anticontamination cover 1 and the gastrostomy catheter 6 pass through the mouth, the larynx, the pharynx and the gullet.

The gastrostomy catheter 6 covered with the anticontamination cover 1 is pulled into the stomach 12. At this stage, the base end of the anticontamination cover 1 and the dome 8 at the outer end of the gastrostomy catheter 6 are outside the patient's mouth as shown in FIG. 10.

Then, the sheath 15 is held stationary and the guide wire 17 extending outside from the abdomen is pulled to bring the knot 19 formed by tying the guide wire 17, the gastrostomy catheter 6 and the anticontamination cover 1 into contact with the inner end of the sheath 15.

Figure 11:
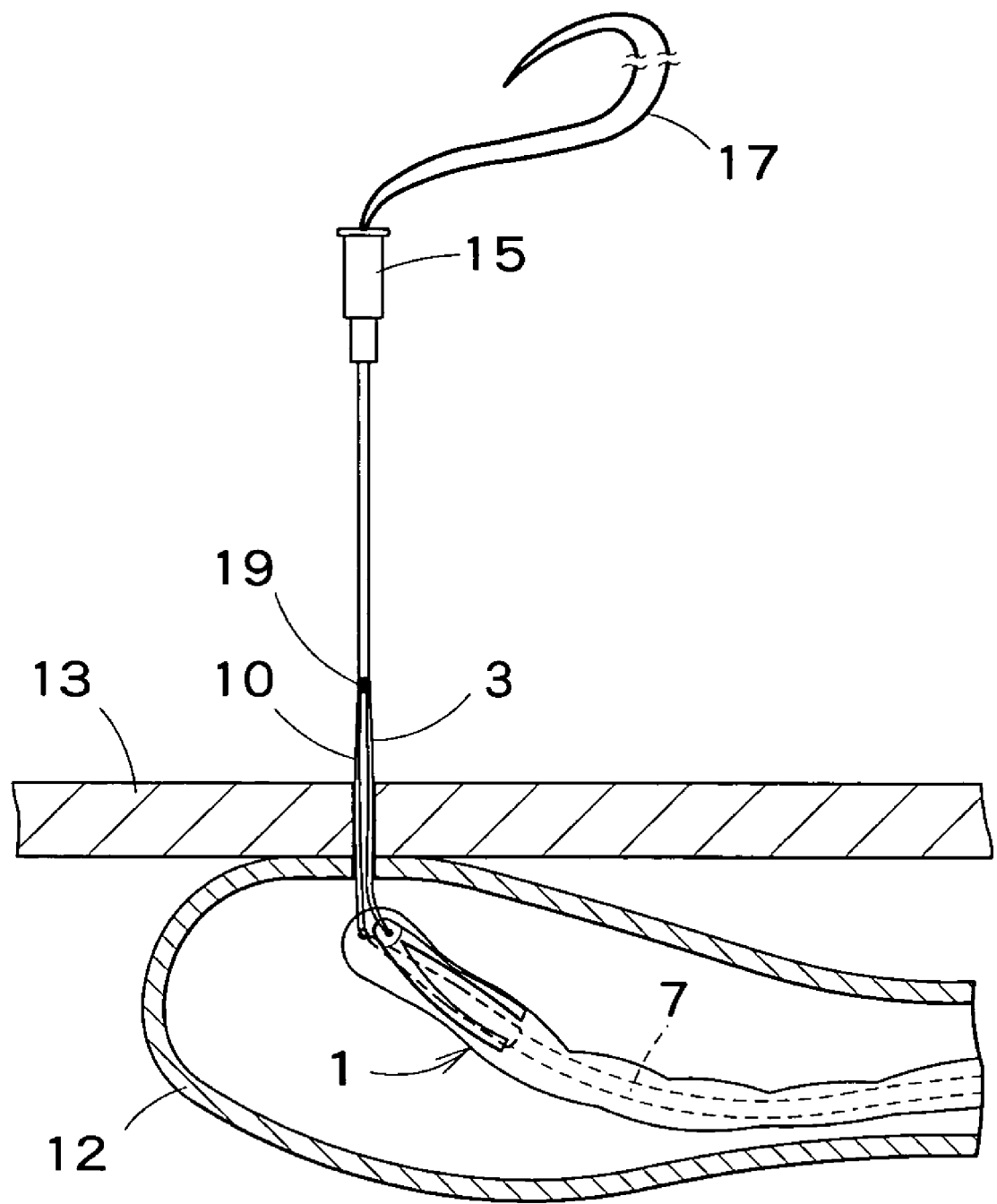
FIG. 11 is a pictorial view showing a state where the joint of the guide wire, the anticontamination cover and the gastrostomy catheter has been pulled outside the body.
Figure 12:
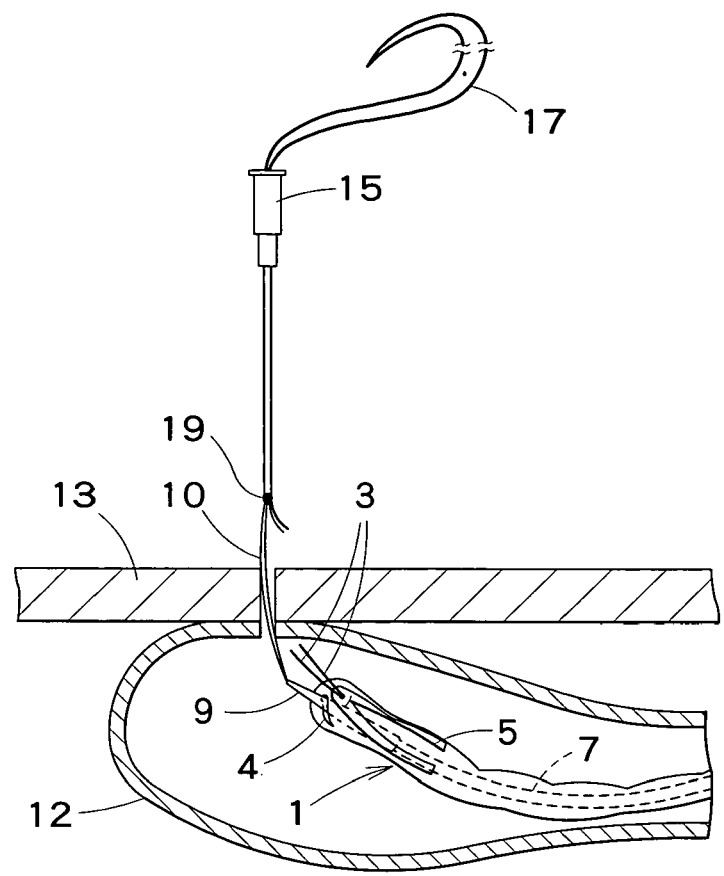
FIG. 12 is pictorial view showing a state where the loop of the anticontamination cover has been cut off the joint of the guide wire, the anticontamination cover and the gastrostomy catheter.
Figure 13:
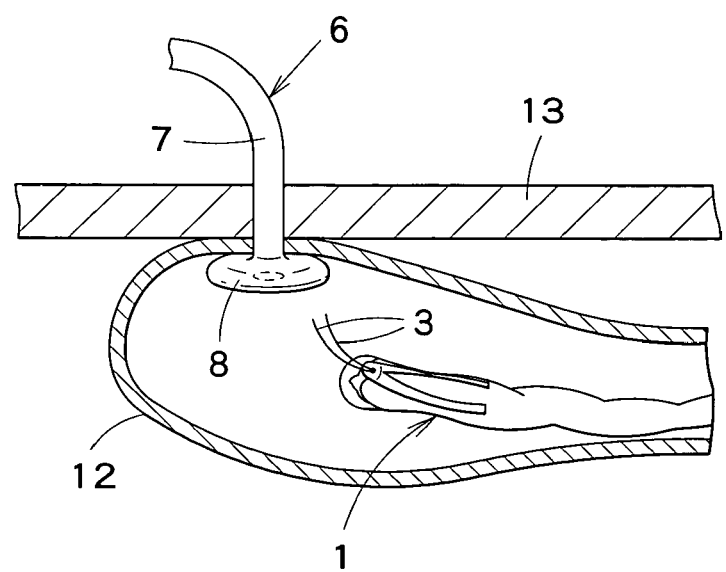
FIG. 13 is a pictorial view showing the gastrostomy catheter placed in a gastric fistula.

After the knot 19 formed by tying the guide wire 17, the gastrostomy catheter 6 and the anticontamination cover 1 has been brought into contact with the inner end of the sheath 15, the guide wire 17 is pulled further outward to pull the knot 19 together with the sheath 15 through the gastric fistula outside the patient's body as shown in FIG. 11.

After the knot 19 has been pulled through the gastric fistula outside the patient's body, the wire loop 10 of the gastrostomy catheter 6 and the loop 3 of the anticontamination cover 1 are gripped with a tool and only a part near the surface of the patient's body of the anticontamination cover 1 is cut with a cutter.

Then, the base end of the anticontamination cover 1 extending outside from the mouth is pulled outside by a length in the range of 4 to 5 cm. At this stage, the cut end of the loop 3 of the anticontamination cover 1 lies in the stomach 12 and is separated from the abdominal wall 13 and the edge of the opening 4 of the anticontamination cover 1 is torn slightly by the dilator 9 of the gastrostomy catheter 6. Then the dilator 9 and the tube can pass the thus expanded opening 4.

Subsequently, the knot 19 is held by hand and the tube 7 of the gastrostomy catheter 6 is pulled outside the patient's body through the gastric fistula. The base part of the anticontamination cover 1 extending outside from the patient's mouth is held by hand while the knot 19 is being pulled to restrain the anticontamination cover 1 from being pulled into the patient's body.

Since the anticontamination cover 1 is held stationary while the knot 19 is being pulled in a direction away form the patient's body, the dilator 9 connected to the knot 19 is pulled into the stomach 12 tearing the edge of the opening 4, and then the tube 7 continuous with the dilator 9 is pulled into the stomach 12.

Then, the tube 7 of the gastrostomy catheter 6 pulled into the stomach 12 is pulled further to pull the tube 7 through the gastric fistula outside the patient's body. Finally, the dome 8 formed at the end of the tube 7 is pulled out through the torn opening 4 from the anticontamination cover 1 and is brought into contact with the inner surface of the gastric wall 12a. Then, the base end of the anticontamination cover 1 is held by hand and the anticontamination cover 1 is pulled outside the patient's body through the mouth. The endoscope 20 is inserted through the mouth into the stomach 12 to confirm that the dome 8 of the gastrostomy catheter 6 is in contact with the inner surface of the gastric wall 12a.

The tube 7 of the gastrostomy catheter 6 extending outside the patient's body is cut in a proper length. The tube 7 is fastened to the patient's body by a fastening device, not shown, to complete the surgical operation for gastrostomy.

As apparent from the foregoing description, the anticontamination cover according to the present invention covering the gastrostomy catheter 6 is inserted by way of the mouth, the larynx, the pharynx and the gullet into the stomach. Therefore, the gastrostomy catheter is not contaminated with bacteria adhering to the mouth, the larynx, the pharynx and the gullet.

The edge of the opening formed in the anticontamination cover at a position apart from the loop can be easily torn. Therefore, the gastrostomy catheter will not be contaminated with bacteria adhering to the loop when the gastrostomy catheter is pulled out of the anticontamination cover.

Although the invention has been described in its preferred embodiment with a certain degree of particularity, obviously many changes and variations are possible therein. It is therefore to be understood that the present invention may be practiced otherwise than as specifically described herein without departing from the scope and spirit thereof.

What is claimed is:

1. An anticontamination cover, for covering a gastrostomy catheter, comprising:

an elongate covering tube having a closed distal end and an open base end; and a loop attached to and projecting from the outside surface of the distal end of the covering tube;

wherein an opening is formed in a part of the distal end of the covering tube opposite a part of the distal end to which the loop is attached to pass a wire loop of the gastrostomy catheter inserted in the covering tube therethrough, the attached loop projecting from the outside surface of the covering tube such that the attached loop can be aligned, together with the wire loop passed through the opening, and the attached loop and wire loop can be connected with a guide wire passing through the attached loop and wire loop at the same position on the guide wire, and such that the attached loop can be cut without cutting the wire loop when the attached loop and the wire loop are pulled by the guide wire from a patient's body, and wherein the opening formed in the part of the distal tube is tearable such that the gastrostomy catheter can be torn from the covering tube by pulling the gastrostomy catheter from the elongate covering tube with the guide wire connected to the wire loop.

2. The anticontamination cover according to claim 1, wherein the loop is formed by looping a synthetic resin filament.

3. The anticontamination cover according to claim 1, wherein the covering tube is formed from an easily breakable synthetic resin film.

4. The anticontamination cover according to claim 3, wherein the loop is formed by looping a synthetic resin filament.

5. The anticontamination cover according to claim 1, wherein the opening is formed in a part of the distal end of the covering tube opposite a part of the distal end of the covering tube to which loop is attached.

6. The anticontamination cover according to claim 5, wherein the loop is formed by looping a synthetic resin filament.

7. The anticontamination cover according to claim 5, wherein the covering tube is formed from an easily breakable synthetic resin film.

8. The anticontamination cover according to claim 7, wherein the loop is formed by looping a synthetic resin filament.

9. An apparatus comprising:
(a) a gastrostomy catheter comprising a tube, a dome formed in a first end of the tube, a dilator at an opposite end of the tube, and a wire loop connected to the dilator;
(b) the anticontamination cover according to claim 1, wherein the anticontamination cover covers the gastrostomy catheter with the wire loop of the catheter extending through the opening in the distal end of the anticontamination cover; and
(c) a guide wire, the attached loop and the wire loop being connected with the guide wire at the same position on the guide wire.

10. An anticontamination cover for covering a gastrostomy catheter, wherein the gastrostomy catheter includes a tube, a dome formed in a first end of the tube, a dilator at an opposite end of the tube, and a wire loop connected to the dilator, the anticontamination cover comprising:
(a) an elongate covering tube having a distal end and a base end, the base end being open, the distal end being closed except for an opening through which the wire loop of the catheter extends when the anticontamination cover is covering the gastrostomy catheter, the covering tube and opening being constructed to tear when the dilator of the gastrostomy catheter is pulled through the opening;
(b) a filament; and
(c) means for attaching the filament to an outside surface of the covering tube to form an attached loop that has (a) a periphery having a first portion attached to the outside surface of the covering tube at a portion of the distal end opposite the opening, a remainder of the periphery being disposed outside of the covering tube, and (b) an aperture defined by the periphery that is disposed such that, when the anticontamination cover covers the gastrostomy catheter with the wire loop of the catheter extending through the opening in the distal end of the anticontamination cover, a guide wire can pass through both the wire loop and the aperture of the attached loop and connect the wire loop and the attached loop at the same position of the guide wire for pulling the gastrostomy catheter covered by the anticontamination catheter through the mouth, larynx, pharynx and stomach of a patient.

11. The anticontamination cover according to claim 10, wherein the means for attaching comprises an adhesive strip.

12. The anticontamination cover according to claim 10, wherein the means for attaching comprises a welded film.

13. An apparatus comprising:
(a) a gastrostomy catheter comprising a tube, a dome formed in a first end of the tube, a dilator at an opposite end of the tube, and a wire loop connected to the dilator;
(b) the anticontamination cover according to claim 10, wherein the anticontamination cover covers the gastrostomy catheter with the wire loop of the catheter extending through the opening in the distal end of the anticontamination cover; and
(c) a guide wire, the attached loop and the wire loop being connected with the guide wire at the same position on the guide wire.

14. A kit comprising:
(a) a gastrostomy catheter comprising a tube, a dome formed in a first end of the tube, a dilator at an opposite end of the tube, and a wire loop connected to the dilator; and
(b) the anticontamination cover according to claim 10.

15. An apparatus comprising:
(a) a gastrostomy catheter comprising a tube, a dome formed in a first end of the tube, a dilator at an opposite end of the tube, and a wire loop connected to the dilator; and
(b) the anticontamination cover according to claim 10, wherein the anticontamination cover covers the gastrostomy catheter with the wire loop of the catheter extending through the opening in the distal end of the anticontamination cover.

16. A kit comprising:
(a) a gastrostomy catheter comprising a tube, a dome formed in a first end of the tube, a dilator at an opposite end of the tube, and a wire loop connected to the dilator; and
(b) the anticontamination cover according to claim 11.

17. A kit comprising:
(a) a gastrostomy catheter comprising a tube, a dome formed in a first end of the tube, a dilator at an opposite end of the tube, and a wire loop connected to the dilator; and
(b) the anticontamination cover according to claim 12.

18. An anticontamination cover for covering a gastrostomy catheter that comprises a wire loop portion and a dome portion, the anticontamination cover comprising an elongate covering tube having an open base end and a distal end; the distal end being closed except for tearable opening means for permitting passage of the wire loop portion of the catheter without permitting passage of the dome portion of the catheter unless and until the opening means is torn by the dome portion of the catheter being pulled through the opening means, the distal end comprising loop means for forming a loop projecting from the elongate covering for aligning with the wire loop portion of the catheter so that a guide wire can engage the aligned loop and wire loop portion together and pull them through the body of a patient, the loop means being separated from the tearable opening means such that the catheter does not contact the loop means when the opening is torn and the dome portion of the catheter is pulled through the opening.

19. A kit comprising:
(a) a gastrostomy catheter comprising a tube, a dome formed in a first end of the tube, a dilator a an opposite end of the tube, and a wire loop connected to the dilator; and
(b) the anti-contamination cover according to claim 18, wherein the opening means comprises an opening that is sized such that the dome portion of the catheter can pass through the opening if and only if the opening is torn.

* * * * *